(12) United States Patent
Feith

(10) Patent No.: US 11,400,211 B2
(45) Date of Patent: Aug. 2, 2022

(54) PRESSURE SPIKE ABSORBING SYSTEMS

(71) Applicant: CareFusion Corporation, San Diego, CA (US)

(72) Inventor: Raymond Feith, Chino Hills, CA (US)

(73) Assignee: CAREFUSION CORPORATION, San Diego, CA (US)

( * ) Notice: Subject to any disclaimer, the term of this patent is extended or adjusted under 35 U.S.C. 154(b) by 337 days.

(21) Appl. No.: 15/807,475

(22) Filed: Nov. 8, 2017

(65) Prior Publication Data
US 2019/0134304 A1 May 9, 2019

(51) Int. Cl.
| | | |
|---|---|---|
| *A61M 5/168* | (2006.01) | |
| *F16L 55/052* | (2006.01) | |
| *F16L 55/054* | (2006.01) | |
| *A61M 5/14* | (2006.01) | |
| *F04B 11/00* | (2006.01) | |

(52) U.S. Cl.
CPC .......... *A61M 5/16831* (2013.01); *A61M 5/14* (2013.01); *A61M 5/16804* (2013.01); *F16L 55/052* (2013.01); *F16L 55/054* (2013.01); *A61M 5/16877* (2013.01); *A61M 2005/1405* (2013.01); *A61M 2205/3341* (2013.01); *F04B 11/00* (2013.01)

(58) Field of Classification Search
CPC .......... A61M 5/16831; A61M 5/16804; A61M 5/16877; A61M 2205/3341; A61M 5/152
See application file for complete search history.

(56) References Cited

U.S. PATENT DOCUMENTS 2,838,073 A * 6/1958 Bruce ................... F16L 55/052
138/30
3,095,120 A   6/1963 Steiner et al.
(Continued)

FOREIGN PATENT DOCUMENTS

CN    1211453 A    3/1999
EP    0900099 A1   3/1999

OTHER PUBLICATIONS

International Search Report and Written Opinion for Application No. PCT/US2018/059649, dated Mar. 18, 2019, 14 pages.
(Continued)

*Primary Examiner* — Dung T Ulsh
(74) *Attorney, Agent, or Firm* — Morgan, Lewis & Bockius LLP

(57) ABSTRACT

An apparatus for coupling to a fluid delivery system and for receiving a fluid into the apparatus; a portion of the apparatus permitting a change in shape or size to accommodate the fluid volume or pressure received therein. The apparatus including a housing with a cavity, an expandable reservoir with an opening and a passage, and a cap; the expandable reservoir positioned within the cavity and coupled to a fluid source. The expandable reservoir includes an unrestrained orientation when a fluid volume or pressure therein is below a threshold, and an expanded orientation, when the fluid volume or pressure therein is above the threshold; the expandable reservoir moving toward the expanded orientation to accommodate a fluid volume or pressure received through an opening, and the expandable reservoir moving toward the unrestrained orientation to direct a fluid volume or pressure through an opening.

18 Claims, 6 Drawing Sheets

(56) References Cited

U.S. PATENT DOCUMENTS

| | | | | |
|---|---|---|---|---|
| 4,514,295 A | * | 4/1985 | Mathieu | A61M 1/30 |
| | | | | 210/321.65 |
| 5,697,919 A | | 12/1997 | Kinoshita et al. | |
| 2009/0247950 A1 | * | 10/2009 | Tsukada | A61M 5/152 |
| | | | | 604/132 |
| 2016/0106916 A1 | * | 4/2016 | Burmaster | A61M 5/16804 |
| | | | | 604/28 |

OTHER PUBLICATIONS

International Preliminary Report on Patentability from International Preliminary Examining Authority for Application No. PCT/US2018/059649, dated Nov. 8, 2019, 15 pages.

Chinese Office Action for Application No. 201880072113.9, dated Jul. 5, 2021, 18 pages including machine translation.

European Office Action for Application No. 18807527.9, dated May 21, 2021, 5 pages.

\* cited by examiner

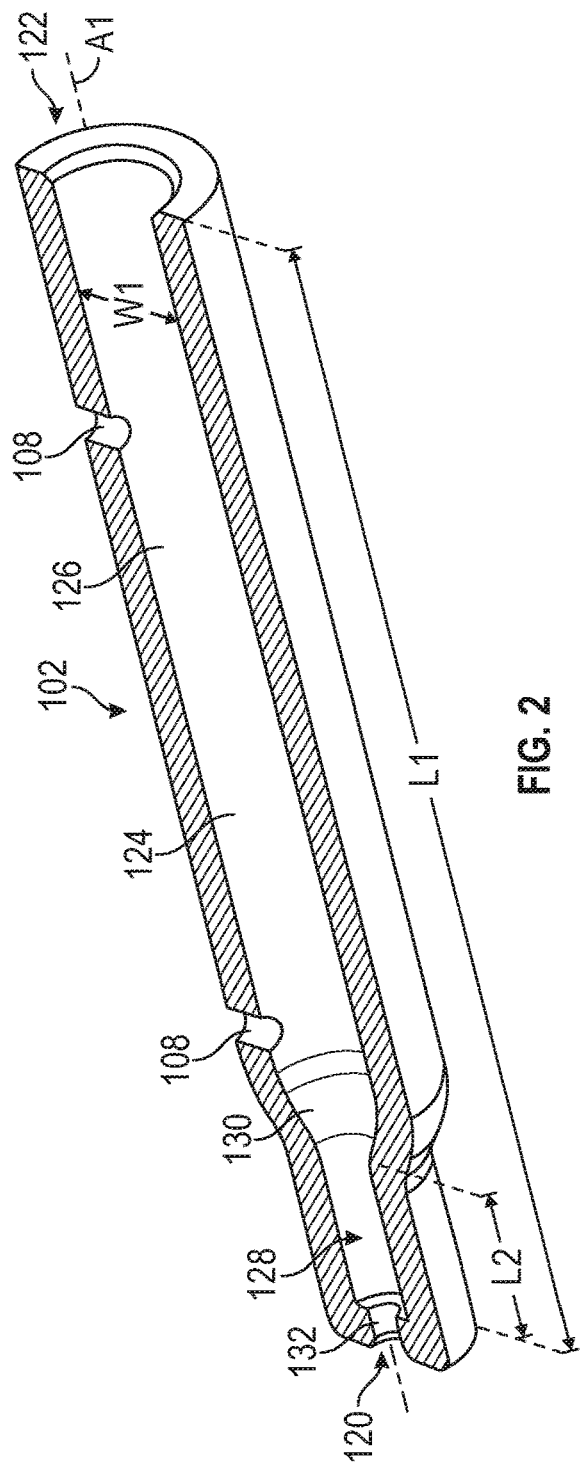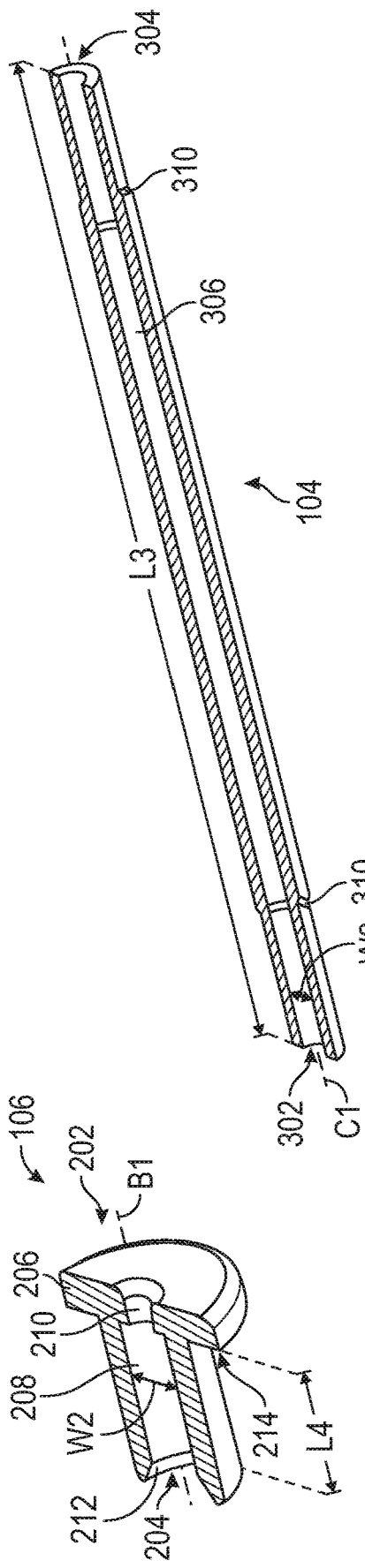

PRESSURE SPIKE ABSORBING SYSTEMS

BACKGROUND

The present inventions relate to systems for providing safe management of fluid pressure within intravenous (IV) therapy tubing. More specifically, to devices and methods for capturing and dispensing fluid pressure bolus in an IV set.

IV infusion is used to administer an IV fluid into a vein of patient by means of tubing fluidly coupled to a vein of the patient. The IV fluids are infused through flexible, plastic tubing connected to a source of fluid at one end and to the hub of an IV catheter or extension tubing at the other end. The plastic tubing is often a portion of an IV set that includes IV tubing, an access port, and an outlet port. The IV set can be coupled with a fluid source, which can be an IV bag with a fluid therein. The fluid can be a medicament to be directed from the fluid source to the patient's vein through the IV set. The fluid can be injected into the patient through a needle or catheter coupled to the outlet port of the IV set. It should be understood that the pressure spike absorbing system of the present disclosure can be used with an IV set or any fluid delivery system.

An access port coupled with the IV tubing can be utilized to administer additional or a different fluid to the patient. For example, a medicament can be injected into the IV tubing to achieve a bolus. An IV bolus is commonly used when rapid administration of a medication is needed, such as in an emergency; when drugs that cannot be diluted, such as many cancer chemotherapeutic drugs, are administered; and when the therapeutic purpose is to achieve a peak drug level in the bloodstream of the patient. An IV bolus can also be utilized when an IV drip is not necessary and/or possible.

To achieve an IV bolus, a caregiver fluidly couples a fluid source with the IV tubing. For example, a syringe can be coupled to the IV tubing through an access port. The caregiver pushes the plunger of the syringe for a period of time to inject a fluid from the syringe into the IV tubing. The IV tubing can be referred to as microbore tubing, which can have an inner diameter of about 10 mm or less. Because the IV tubing creates a restriction to the flow of fluid being injected, the caregiver must push the syringe plunger with a greater level of force and for a longer period of time relative to injection of a fluid into tubing having a larger inner diameter or inner volume. The greater level of force, and longer period of time, required to inject the fluid requires increased physical exertion by the caregiver. Further, the level of force and period of time may increase relative to the viscosity of the fluid being injected.

The IV bolus can create a pressure spike within the IV set, relative to a normal pressure within the IV set. For example, one pound of force applied to the plunger of a one cubic centimeter syringe can generate output of 40 pounds per square inch by the syringe. The pressure is directed into the IV set where it can cause the physical integrity of the IV set to fail, resulting in a leak of the IV tubing or other portion of the IV set.

SUMMARY

In accordance with at least some embodiments disclosed herein is the realization that although a fluid can be injected into an IV set, certain problems occur when a bolus occurs within an IV set. For example, a pressure spike within the IV set can damage a portion of the IV set and cause a leak, losing valuable medicament, and potentially exposing a caregiver and/or patient to harmful substances.

Some embodiments disclosed herein relate to the realization that when fluid is injected into an IV set, a caregiver must inject the fluid from the syringe over a period of time. The time required to inject the fluid from the syringe prevents a busy caregiver from attending to other tasks or patients.

Embodiments disclosed herein also relate to the realization that when a caregiver must exert significant physical stress to push the syringe plunger into the syringe and overcome the flow restriction of the IV tubing. A caregiver may repeat this process multiple times per work shift, and for multiple patients, thereby exacerbating the required physical exertion and causing injury to the caregiver.

Accordingly, in some embodiments, a pressure spike absorbing device is provided that prevents damage to an IV set caused by an IV bolus. For example, some embodiments can reduce the pressure spike of a bolus within an IV set. As such, the present disclosure permits the capturing of fluid injected into an IV set such that the increased pressure is diverted from other portions of the IV set.

In some embodiments, a pressure spike absorbing device is provided that permits dispensing of the captured fluid from the pressure spike absorbing device at a consistent rate and/or pressure. As such, the present disclosure provides a predictable rate of introduction of the injected fluid into the IV set or to the patient.

In some embodiments, a pressure spike absorbing device is provided that prevents injury to a caregiver injecting a fluid into an IV set. For example, some embodiments can reduce the force required to inject a fluid into an IV set. As such, the fluid injected into the IV set can be received into a device of the present disclosure, which provides less resistance to an increase in pressure relative to other portions of the IV set and/or IV tubing.

Additionally, some embodiments of the present disclosure can provide interchangeable modular portions of the system to achieve specific characteristics. For example, interchangeable housings and/or expandable reservoirs can be combined to achieve a desired size or shape. As such, interchangeable portions of the system can be selected to couple with IV tubing having a specific cross-sectional width and/or shape profile.

Further, interchangeable housings and/or expandable reservoirs can be combined to achieve a desired system performance. As such, interchangeable portions of the system can be selected to have any of a specific fluid capacity of the housing and/or expandable reservoir, a specific rate of expansion of the expandable reservoir, and a specific rate of compression of the expandable reservoir.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings.

The illustrated embodiments are intended to illustrate, but not to limit, the inventions. The drawings contain the following figures:

FIG. 2 is a cross-sectional view of a housing of a pressure spike absorbing system, according to some embodiments.

FIG. 3 is a cross-sectional view of a cap of a pressure spike absorbing system, according to some embodiments.

FIG. 4 is a cross-sectional view of an expandable reservoir of a pressure spike absorbing system, according to some embodiments.

DETAILED DESCRIPTION

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings, and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Although the pressure spike absorbing system 100 can be used with an intravenous fluid delivery system such as an IV set, it should be appreciated that the pressure spike absorbing system 100 can be used with other fluid delivery systems. However, for clarity and brevity, the present disclosure will primarily refer to an IV set.

Figure 1:
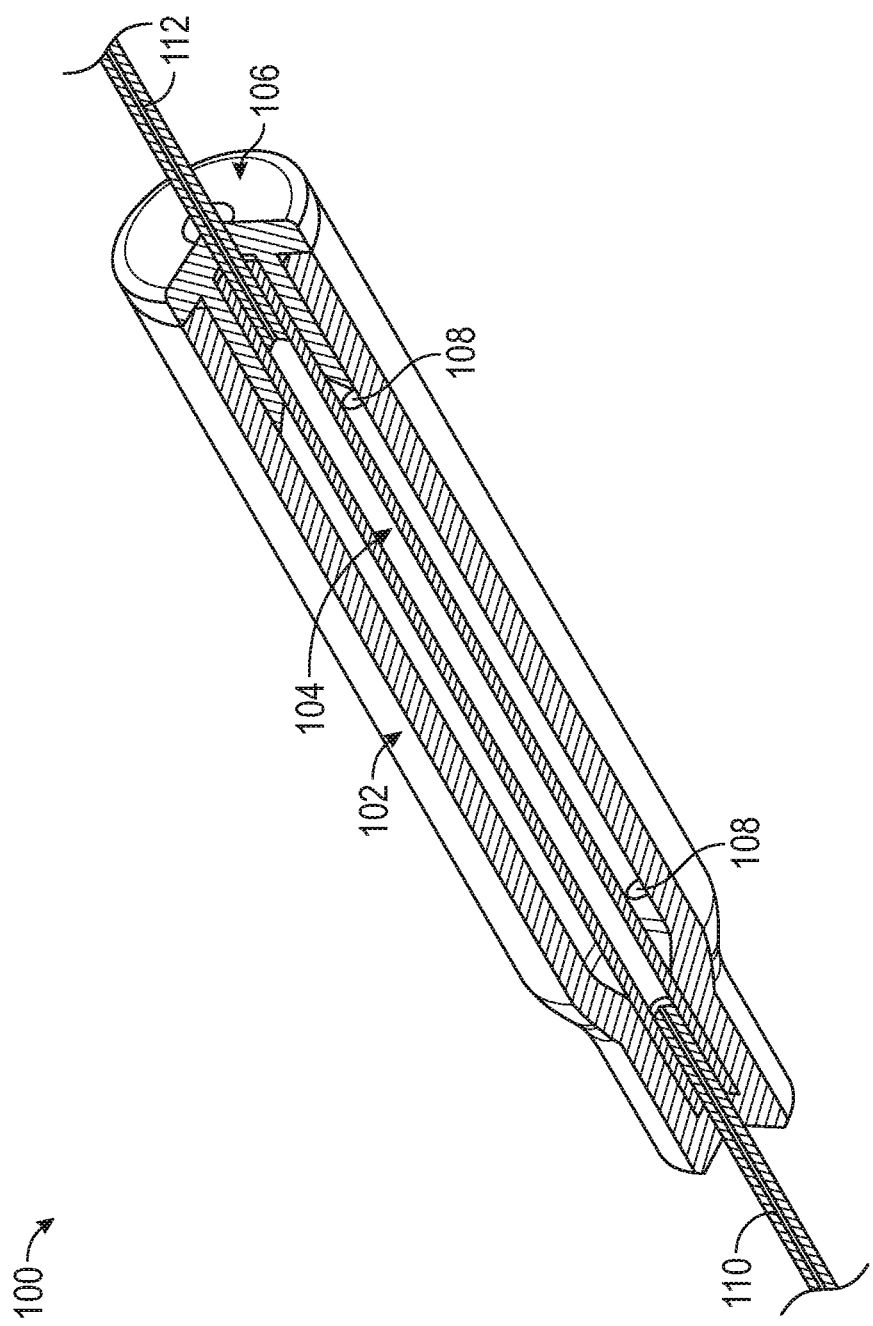
FIG. 1 is a cross-sectional perspective view of a pressure spike absorbing system coupled with tubing, according to some embodiments.

FIG. 1 illustrates a pressure spike absorbing system 100 according to some embodiments of the present disclosure. The pressure spike absorbing system 100 can comprise a housing 102, an expandable reservoir 104, and a cap 106.

The pressure spike absorbing system 100 is coupled with a first portion of a tubing 110 and second portion of a 112.

In some embodiments of the present disclosure, a vent passage 108 of the pressure spike absorbing system 100 permits a gas to exit and enter a cavity of the housing 102 during expansion and contraction of the expandable reservoir 104.

When a fluid is injected into the tubing 110 and 112, for example, when a medicament is injected into an IV set to introduce the medicament into an IV drip, the pressure within the IV set increases due to an increase in fluid volume within the IV set. The increased pressure can be received by the pressure spike absorbing system 100, wherein the expandable reservoir 104 can provide less resistance to the pressure than other portions of the IV set.

The pressure causes the expandable reservoir 104 to expand and the inner volume therein to increase. The increased inner volume of the expandable reservoir 104 accommodates the increase in fluid volume. By accommodating the increase in fluid volume, and thus the increase in pressure, the pressure spike absorbing system 100 reduces the resistance to flow during injection of the fluid into the IV set and prevents the increase in pressure from causing damage to other portions of the IV set.

FIG. 2 illustrates a cross-sectional view of a housing 102 of the pressure spike absorbing system 100. The housing 102 is configured to receive at least a portion of the expandable reservoir 104 within a cavity of the housing. The housing 102 can limit expansion of the expandable reservoir 104, and can protect the expandable reservoir 104 from unintentional contact with a foreign object, which can damage or affect performance of the expandable reservoir 104.

The housing 102 can include a first portion 120, a second portion 122, a cavity 126, a first retaining bore 128, and a first tubing passage 132. The first portion 120 and the second portion 122 can comprise opposite portions of the housing 102. In some embodiments, the first portion 120 and the second portion 122 can be positioned adjacent to each other.

The housing 102 can be shaped as a tube or cylinder, and can have a cross-sectional profile that includes a regular or irregular shape. For example, the cross-sectional profile can include any of a circle, oval, square, rectangle, triangle, or combination thereof. The housing 102 can be formed monolithically, as single piece, or can be formed of multiple pieces coupled together.

The housing 102 can be configured to limit the volume of fluid received into the pressure spike absorbing system 100 by restricting expansion of the expandable reservoir 104. To limit the volume of fluid received into the system 100, the housing 102 can have a size that corresponds to a volume of fluid to be received by the pressure spike absorbing system 100. For example, a pressure spike absorbing system 100 that is intended to receive a small volume of fluid can be configured with a smaller expandable reservoir 104 compared to a pressure spike absorbing system 100 that is intended to receive a relatively larger volume of fluid. Thus, a pressure spike absorbing system 100 intended to receive a smaller expandable reservoir 104 can have a smaller housing 102 relative to a pressure spike absorbing system 100 intended to receive a larger expandable reservoir 104.

An inner surface 124 of the housing can form a cavity 126 for the expandable reservoir. The cavity 126 can be formed within a portion of the housing 102, and is configured to extend around an outer surface of the expandable reservoir 104, or a portion thereof. The cavity 126 can extend from the second portion 122 of the housing toward the first portion 120 of the housing. The cavity 126 can extend from an end of the housing 102 at the first or second portion 120 or 122, toward the other of the first or second portion 120 or 122. In some embodiments, the cavity 126 extends between the first portion 120 and the second portion 122. Further, the cavity 126 can extend through any of the first portion 120 and the second portion 122 of the housing 102.

The cavity 126 can have a length L1 that extends between the first portion 120 and the second portion 122. The length L1 can be at least about 1.0 inch and/or less than or equal to about 6.0 inches. Further, the length L1 can also be between about 2.0 inches and about 4.0 inches.

The cavity 126 can have a cross-sectional profile that is transverse to a housing axis A1 that extends between the first portion 120 and the second portion 122. The cross-sectional profile of the cavity 126 can includes a regular or irregular shape. The shape of the cross-sectional profile can include any of a circle, oval, square, rectangle, triangle, or combination thereof. The cross-sectional profile of the cavity 126 can have a width W1 that extends between opposing inner surfaces of the cavity. The width W1 can be at least about 0.25 inch and/or less than or equal to about 2.0 inches. Further, the width W1 can also be between about 0.5 inch and 1.0 inch.

The size of the cavity 126 can be described by a volume defined by the inner surface 124 of the housing that forms the cavity 126. The cavity 126 can have a volume of at least about 0.25 cc and/or less than or equal to about 15 cc. Further, the capacity can also be between about 1 cc and about 6 cc.

When an expandable reservoir 104 is positioned within the housing 102, the space between an outer surface of the expandable reservoir 104, in an unrestrained orientation, and the inner surface of the housing 102 defines a differential capacity. The differential capacity can designate the volume, which the pressure spike absorbing system 100 is intended to accommodate. The differential capacity can be at least about 0.25 cc and/or less than or equal to about 10 cc, or between about 0.5 cc and about 5 cc. In some embodiments of the present disclosure, the differential capacity is 3 cc.

In some aspects of the present disclosure, the volume or differential capacity of the cavity 126 can be a ratio relative to a volume of the expandable reservoir 104. For example, the volume or differential capacity of the cavity can be can be at least about 10% and/or less than or equal to about 150% larger than the volume of the expandable reservoir 104. Further, the volume or differential capacity of the cavity can be can be between about 25% and about 50% larger than the volume of the expandable reservoir 104.

A first retaining bore 128 of the housing 102 is configured to receive a portion of the expandable reservoir 104. The first retaining bore 128 retains a portion of the expandable reservoir 104, and restricts movement of the expandable reservoir relative to the housing 102.

The first retaining bore 128 can be formed by an inner surface of the housing 102. The first retaining bore 128 extends from the cavity 126 toward the first portion 120 of the housing. In some embodiments of the present disclosure, the first retaining bore 128 can extend from the cavity 126 through an outer surface of the housing 102.

The first retaining bore 128 can have a shape, or cross-sectional profile, that corresponds with a shape of the expandable reservoir 104. For example, the cross-sectional profile of the first retaining bore 128 can be the same or about the same as a cross-sectional profile of an outer surface of the expandable reservoir 104. The first retaining bore 128 can have a length L2 that extends between the cavity 126 and the first portion 120 of the housing 102. The length L2 of the retaining bore corresponds to a length of the expandable reservoir 104 that can be retained therein. In some embodiments, the length L2 of the retaining bore is a ratio relative to length L3 of the expandable reservoir 104. For example, the length L2 of the retaining bore 128 can be at least about 1% and/or less than or equal to about 49% of the length L3 of the expandable reservoir 104. Further, the length L2 of the retaining bore can also be between about 20% and about 30% of the length L3 of the expandable reservoir 104.

When an expandable reservoir 104 is coupled with the pressure spike absorbing system 100, the a portion of the expandable reservoir 104 is positioned within the first retaining bore 128. The expandable reservoir 104 is positioned within the first retaining bore 128 so that the outer surface of the expandable reservoir engages against the inner surface of the housing along the first retaining bore 128. The engagement between the expandable reservoir 104 and the first retaining bore 128 resists movement of the expandable reservoir 104 relative to the housing 102. The first retaining bore 128 can resists movement of the expandable reservoir 104 along the housing axis A1, and/or can resist rotational movement of the expandable reservoir 102 around the housing axis A1.

In some embodiments of the present disclosure, a first retaining bore extends from the cavity 126 toward the first portion 120 of the housing, and a second retaining bore extends from the cavity 126 toward the second portion 122 of the housing.

The housing 102 can include a transition surface 130 between the cavity and the retaining bore to prevent damage to the expandable reservoir 104 during expansion of the reservoir and return of the expandable reservoir to an unrestrained orientation. The transition surface 130 forms a gradual transition between an inner surface of the housing at the cavity and an inner surface of the housing at the first retaining bore 128. The gradual transition of the inner surface of the housing 102 reduces the likelihood of creating a stress point on an expandable reservoir engaged against the housing 102.

The transition surface 130 can be formed by an inner surface 124 of the housing 102 between the cavity 126 and the first retaining bore 128. The transition surface 130 can be shaped with a cross-sectional width that tapers between the cavity 126 and the first retaining bore 128. The cross-sectional width of the inner surface 124 can taper from the cavity 126 toward the first retaining bore 128. In some aspects of the present disclosure, a cross-sectional width of the cavity 126 is greater than a cross-sectional width of the first retaining bore 128, such that the inner surface 124 tapers from the cavity 126 toward the first retaining bore 128.

A first tubing passage 132 of the housing 102 can permit a portion of tubing to extend into the housing 102. The first tubing passage 132 provides a passage through the housing to permit an IV tubing to be moved through the housing and coupled with any of the housing 102 and the expandable reservoir 104.

The first tubing passage 132 extends between the cavity 126 and an outer surface of the housing 102. The first tubing passage 132 can extend from the first retaining bore 128 toward the first portion 120 of the housing. The first tubing passage 132 can be aligned with the first retaining bore 128 so that a passage extends through each of the first tubing passage 132 and the first retaining bore 128. In some aspects of the present disclosure, the axis A1 extends through the first tubing passage 132 and the first retaining bore 128.

In some embodiments of the present disclosure, the first tubing passage 132 is positioned between the first portion 120 and the second portion 122 of the housing, and extends from the cavity 126 to an outer surface of the housing 102.

The first tubing passage 132 can have a cross-sectional width that permits a tubing inserted therethrough to move relative to the housing 102. In some embodiments of the present disclosure, the first tubing passage 132 includes a cross-sectional width that is about the same cross-sectional width of the tubing, thereby providing an interference fit between the tubing and the first tubing passage 132.

In some aspects, the cross-sectional profile of the first tubing passage 132 is less than the cross-sectional profile of the expandable reservoir 104. Thus, when the IV tubing is moved in a direction away from the housing, the portion of the expandable reservoir 104, coupled to the IV tubing, engages against the housing to resist retraction of the IV tubing or separation of the IV tubing from the pressure spike absorbing system 100.

In some embodiments of the present disclosure, the housing 102 comprises a ventilation passage 108. The ventilation passage 108 permits a gas to move into and out of the housing 102. A gas can be displaced from the housing 102 when the expandable reservoir 104 increases in size, or moves toward an expanded orientation. When the expandable reservoir retracts, or moves toward an unrestrained orientation, the ventilation passage 108 permit a gas to move into the housing 102.

The ventilation passage 108 can be shaped as an opening that extends through the housing. The ventilation passage 108 can extend between an inner surface of the housing and an outer surface of the housing. In some embodiments of the present disclosure, the ventilation passage 108 extends from the cavity to an outer surface of the housing.

A portion of the ventilation passage 108 can be positioned along a portion of the housing 102 forming the cavity 126, thereby permitting a gas to move toward or away from the housing. In some embodiments of the present disclosure, the pressure spike absorbing system 100 comprises more than one ventilation passage 108. For example, a first ventilation passage 108 can be positioned proximal to the first portion 120 of the housing, and a second ventilation passage 108 can be positioned proximal to the second portion 122 of the housing.

The ventilation passage 108 can be sized to limit the rate of gas moving between the cavity and an atmosphere adjacent the outer surface of the housing. As a result, the ventilation passage 108 can be configured to regulate the rate of expansion of the expandable reservoir 108.

In some embodiments of the present disclosure, the ventilation passage 108 can be any of a passage, a bore, a channel, and a groove that extends between the cavity 126 and an atmosphere adjacent an outer surface of the pressure spike absorbing system 100. The ventilation passage 108 can be a passage that extends through any of the first portion 120 and the second portion 122 of the housing. The ventilation passage 108 can be a channel that extends along a surface of any of the cavity 126, the first retaining bore 128, and the first tubing passage 132. In some aspects, the ventilation passage 108 can be any of a passage that extends through the cap 106, and a channel that extends along a surface of the cap 106.

The housing 102 can comprise a material that is configured to resist deformation during intended use of the pressure spike absorbing system 100. For example, the material of the housing 102 may be rigid relative to the expandable reservoir 104. The housing 102 can be more rigid than the expandable reservoir 104 such that when the expandable reservoir 104 is urged against the housing during expansion, the housing 102 resists changing shape or size. Further, the material of the housing 102 can be selected to limit or prevent expansion of the expandable reservoir 104 beyond a threshold. The material of the housing 102 can be any of a plastic, a metal, a glass, a rubber, a composite, and any combination thereof.

In some embodiments of the present disclosure, the housing 102, or a portion thereof, can permit a change of shape. For example, the material of the housing can be configured to maintain shape of the housing up to a specified pressure and then be urged or biased by the expandable reservoir. A portion of the housing can flex, relative to other portions of the housing, or a portion of the housing can be moveable, relative to other portions of the housing.

The housing 102 can protect the expandable reservoir 104 from damage by preventing contact from a foreign object or person against the expandable reservoir 104. Contact by a sharp or abrasive object against the expandable reservoir 104 may tear, cut, or penetrate the expandable reservoir 104 and cause a leak in the IV set. In another aspect of the present disclosure, the housing 102 can prevent damage to the expandable reservoir 104 by resisting undesired expansion of the expandable reservoir 104, which may cause the expandable reservoir 104 to tear. In yet another aspect of the present disclosure, the housing 102 maintains a shape of the expandable reservoir 104, thereby preventing bending or kinking of the reservoir, which may affect intended performance of the system or damage to the expandable reservoir 104.

The housing 102 is coupled with the expandable reservoir 104 and the cap 106 to form the pressure spike absorbing system 100. The expandable reservoir 104 is positioned within the cavity 126 of the housing, and the cap 106 is coupled to the housing 102 and the expandable reservoir 104. The pressure spike absorbing system 100 can be assembled with a first portion of the expandable reservoir 104, comprising the first opening, positioned in a first retaining bore 128 of the housing. The cap 106 can be coupled with the housing 102 so that a second portion of the expandable reservoir, comprising the second opening, is positioned in a retaining bore of the cap 106. When the pressure spike absorbing system 100 is assembled, a third portion of the expandable reservoir is positioned within the cavity 126.

Referring to FIG. 3, a cross-sectional view of a cap 106 of the pressure spike absorbing system 100 is illustrated. The cap 106 is configured to couple with the housing 102 to enclose the cavity 126 and retain a portion of the expandable reservoir 104. The cap 106 can be coupled with any of an expandable reservoir 104 and an IV tubing to retain the pressure spike absorbing system 100 with the IV tubing. In some embodiments of the present disclosure, a removable cap 106 can permit modular assembly of the pressure spike absorbing system 100. For example, portions of the pressure spike absorbing system 100 can be interchangeably assembled together and assembled with an IV set.

The cap 106 can be shaped as a cover or plug that couples with the housing 102 to enclose the cavity 126 and/or engage the expandable reservoir 104. The cap 106, or portions thereof, can extend over an outer surface and along the inner surface 124 of the housing 102. The cap can also be shaped as a cover that extends over an outer surface of the housing 102.

The cap 106 can include a first end portion 202, and a second end portion 204, opposite the first end portion 202.

In some embodiments of the present disclosure, the cap 106 includes a second retaining bore 208 and a second tubing passage 210 of the pressure spike absorbing system 100. A cap axis B1 extends between the first end portion 202 and the second end portion 204.

The first end portion 202 includes a lip 206 that extends radially outward relative to the cap axis B1. A surface 214 of the lip, facing toward the second end portion 204, can engage against the second portion 122 of the housing.

The first end portion 202 can have a cross-sectional profile that is transverse relative to the cap axis B1. The cross-sectional profile of the first end portion 202 can be the same as a cross-sectional profile of the housing 102 so that an outer radial surface of the lip 206 is flush or aligns with an outer radial surface of the housing 102 when the cap is coupled with the housing 102.

The second end portion 204 of the cap can extend from the first end portion 202. The second end portion 204 can have a cross-sectional profile that is transverse relative to the cap axis B1. The cross-sectional profile of the second end portion 204 can be the same as a cross-sectional profile of the cavity 126 so that an outer radial surface of the second end portion 204 engages against the inner surface 124 of the housing when the cap is coupled with the housing 102. In some embodiments of the present disclosure, the second end portion 204 can have a width W2 that extends between opposing outer surfaces of the cap. The width W2 of the cap can be the same or about the same as the width W1 of the cavity.

Engagement of the second end portion 204 against the housing can resist separation of the cap 106 from the housing 102. The cap 106 can be coupled with the housing 102 by an interference fit between an outer radial surface of the second end portion 204 of the cap and an inner surface 124 of the housing. In some embodiments of the present disclosure, the cap 106 and the housing 102 are coupled together by any of an interference fit, weld, adhesive, and mechanical coupling. For example, the cap 106 can be adhered or welded with the housing 102. In yet another example, the cap 106 and the housing 102 can comprise mating threads, a corresponding pin and groove, or a mechanical coupling.

The cap 106 can include a second retaining bore 208 configured to receive portion of the expandable reservoir 104. The second retaining bore 208 can be configured to provide the same function and features as the first retaining bore 128 described above. Accordingly, some details and function of the retaining bore are not repeated here for brevity.

The second retaining bore 208 can be formed by an inner surface of the cap 106. The second retaining bore 208 extends from an end of the second end portion 204 toward the first end portion 202. In some embodiments of the present disclosure, the second retaining bore 208 can extend through the first end portion 202 and the second end portion 204.

The second retaining bore 208 can function like that of the first retaining bore 128, to receive and/or retain a portion of the expandable reservoir 104. Accordingly, like the first retaining bore 128, the second retaining bore 208 can be shaped with a cross-sectional profile the is the same or about the same as a cross-sectional profile of an outer surface of the expandable reservoir 104.

A length L4 of the second retaining bore 208 can be about the same as the length L2 of the first retaining bore 128. In some embodiments of the present disclosure, the second retaining bore 208 can have a different length or width than the first retaining bore 128. For example, a cap 106 having a second retaining bore length L4 that is greater than the first retaining bore length L2 can be used to receive a longer portion of the expandable reservoir 104 relative to the first retaining bore 128. Similarly, a cap 106 having a second retaining bore length L4 that is less than the first retaining bore length L2 can be used to receive a shorter portion of the expandable reservoir 104 relative to the first retaining bore 128. Using a cap having a longer or shorter second retaining bore length, relative to the retaining first retaining bore length, can reduce or increase, respectively, the portion of the expandable reservoir 104 than can expand.

The cap 106 can include a transition surface 212 to prevent damage to the expandable reservoir 104 during expansion of the reservoir and return of the expandable reservoir to an unrestrained orientation. The transition surface 212 of the cap can be configured to provide the same function and features as the transition surface 130 of the housing described above. Accordingly, some details and function of the transition surface 212 are not repeated here for brevity.

The transition surface 212 can be positioned along a portion of the second retaining bore 208. The transition surface 212 can be shaped as a chamfer along the surface of the second retaining bore 208. In some aspects of the present disclosure, the transition surface 212 is a concaved portion of an end surface of the cap 106

The transition surface 212 can have a cross-sectional width that is greater than the cross-sectional width of the second retaining bore 208. The cross-sectional width of the transition surface 212 tapers from the second end portion 204 toward the first end portion 202 of the cap.

In some embodiments of the present disclosure, the cross-sectional width of the second retaining bore 208 tapers from the second end portion 204 toward the first end portion 202 of the cap. For example, the second retaining bore 208 can have a first cross-sectional width proximal to the second end portion 204 of the cap that is about equal to the cross-sectional width of the cavity 126, and a second cross-sectional width proximal to first end portion 202 that is less than the first cross-sectional width.

The cap 106 can include a second tubing passage 210 that extends through the cap 106 to permit a portion of tubing to extend into the housing 102. The second tubing passage 210 can be configured to provide the same function and features as the first tubing passage 132 described above. Accordingly, some details and function of the retaining bore are not repeated here for brevity.

The second tubing passage 210 extends between first end portion 202 and the second end portion 204 of the cap 106. The second tubing passage 210 can extend from the second retaining bore 208 toward the first end portion 202 of the cap 106. The second tubing passage 210 can be aligned with the second retaining bore 208 so that a passage extends through each of the second tubing passage 210 and the second retaining bore 208. In some aspects of the present disclosure, the axis B1 extends through the second tubing passage 210 and the second retaining bore 208.

The second tubing passage 210 can permit a segment of tubing to be inserted through the cap 106. For example, a portion of IV tubing can be moved through the second tubing passage 210 to couple with a portion of the expandable reservoir 104.

In some embodiments of the present disclosure, the second tubing passage 210 is shaped as a notch or channel that extends through a portion of the cap 106. For example, second tubing passage 210 can be a channel that extends between the first end portion 202 and the second end portion 204 of the cap 106, and from an outer radial surface toward the cap axis B1. In some aspects, the second tubing passage 210 extends through a portion of the housing 102. For example, the second tubing passage 210 can be any of a passage or channel through the second portion 122 of the housing.

The cap 106 can comprise a material that is configured to resist deformation during use of the pressure spike absorbing system 100. For example, the material of the cap 106 can about the same or similar in hardness as the housing 102. In some embodiments of the present disclosure, the cap 102 comprises a material with a hardness that is less than the housing 102 to permit the cap 102 be partially deformed during coupling of the cap 106 with the housing 102, resulting in an interference fit with the housing 102.

When the cap 102 is coupled with the housing 106, the second portion of the expandable reservoir, comprising the second opening, extends into the second retaining bore 208. Accordingly, the first retaining bore 128 can receive a first portion of the expandable reservoir 104, and the second retaining bore 208 can receive a second portion of the expandable reservoir 104. The second retaining bore 208 can prevent movement of the expandable reservoir 104 relative to the housing 102 and cap 106. For example, when portions of an expandable reservoir 104 are positioned within the first retaining bore 128 and the second retaining bore 208, movement of the expandable reservoir 104 along an axis between the first and second retaining bore is limited.

Referring to FIG. 4, a cross-sectional view of an expandable reservoir 104 of the pressure spike absorbing system 100 is illustrated. The expandable reservoir 104 is configured to receive a fluid, such as a liquid or gas, and to deform to expand and accommodate the increase in fluid.

The expandable reservoir 104 can be shaped as a tube having a first opening 302, a second opening 304, and a passage 306 that is in fluid communication with the first and second opening. The passage 306 can extend between the first opening 302 and the second opening 304. The first opening 302 and the second opening 304 are in fluid communication with the passage 306, thereby permitting a fluid to move into and out of the passage 306 through any of the first and second opening. Although the expandable reservoir 104 is illustrated as having a tubular shape, the expandable reservoir and/or cavity can be any regular or irregular shape, including any of a sphere, square, rectangle, and oval.

The expandable reservoir 104 can have a cross-sectional profile transverse to an expandable reservoir axis C1 that extends between the first portion 120 and the second portion 122. The cross-sectional profile can be a circle; however, the cross-sectional profile can also include any of a circle, oval, square, rectangle, triangle, and combination thereof. The cross-sectional profile can be consistent along the length of the expandable reservoir 104, or can change along the length of the expandable reservoir 104.

The passage 306 of the expandable reservoir can have a cross-sectional width W3 that is about equal to a cross-sectional width of the outer surface of the IV tubing to permit a portion of the IV tubing to be moved into the passage 306. To permit an interference fit between the expandable reservoir 104 and the IV tubing, a cross-sectional width W3 of the passage 306 at first opening 302 and the second opening 304, can be the same as the cross-sectional width of the outer surface of the IV tubing.

In some embodiments of the present disclosure, the cross-sectional width W3 of the passage is greater than the cross-sectional width of the outer surface of the IV tubing, such that a gap or space exists between the inner surface of the expandable reservoir 104 and the outer surface of the IV tubing. The gap can permit an adhesive or other joining material to be used to couple the IV tubing with the expandable reservoir 104. In some aspects, the any of the expandable reservoir 104 and the IV tubing can be configured to shrink or expand to permit coupling of the IV tubing with the expandable reservoir 104. For example, a portion of the IV tubing can be inserted through the first or second opening 302 and 304, and then the expandable reservoir 104, or portion having the IV tubing therein, can be reduced in size to engage the IV tubing.

The passage 306 of the expandable reservoir can have a size that permits a volume of fluid to be received therein. The size of the expandable reservoir can be configured to receive a volume when in the unrestrained orientation and/or in the expanded orientation. The volume can be at least about 0.25 cc and/or less than or equal to about 10 cc, or between about 0.5 cc and about 5 cc. In some embodiments of the present disclosure, the passage 306 can have a volume that is 3 cc.

The expandable reservoir 104 comprises a material that is configured to resiliently deform toward an expanded orientation and return to an unrestrained orientation. The permit the expandable reservoir 104 to deform and return to an unrestrained orientation, the material is resilient, or provides some resistance to deformation. For example, the material of the expandable reservoir 104 can have a durometer that permits a specified rate of expansion and/or return of the expandable reservoir 104 to an unrestrained orientation. The material can be configured with a durometer hardness so that when the expandable reservoir 104 is in an expanded orientation, the fluid therein is directed out of the pressure spike absorbing system 100 at a specified rate.

The expandable reservoir 104 can have a first and second opening; however, in some embodiments, the expandable reservoir 104 can have one opening in fluid communication with a passage or cavity. An expandable reservoir having one opening can permit a fluid to enter the passage and cause the expandable reservoir to expand to accommodate an increase in pressure of the IV set. When the force of the expandable reservoir overcomes the fluid pressure therein, the expandable reservoir will return toward the unrestrained orientation and cause the fluid to be directed out of the opening. An upstream flow control valve, positioned between a fluid access port and the expandable reservoir, can prevent backflow of the fluid toward the access port.

In some embodiments of the present disclosure, the expandable reservoir 104, or a portion of the expandable reservoir between the first and second opening 302 and 304, includes any of a bellows and/or folds. For example, in some embodiments, the expandable reservoir 104 can have one or more fold the extends between the first and second opening, along the expandable reservoir axis C1. In another embodiment, one or more fold that extends along the circumference of the passage 306, around the expandable reservoir axis C1. The one or more fold can unfold or expand when pressure is applied to the passage 306 to increase the volume within the expandable reservoir.

In some embodiments of the present disclosure, the expandable reservoir 104 includes a ridge that can resist further movement of the expandable reservoir 104 relative to the housing 102 and/or IV tubing. The ridge can extend away from the outer surface of the expandable reservoir axis C1 to engage against the housing 102. In some embodiments of the present disclosure, a ridge can extend from an inner surface of the expandable reservoir 102 to engage against an IV tubing inserted therein.

In some embodiments of the present disclosure, the expandable reservoir 104 includes an alignment feature 310. The alignment feature 310 can be any of a dimple, indentation, channel, groove, and ridge that permit a portion of the expandable reservoir 104 to change shape and/or direction. For example, the expandable reservoir 104 can have a groove the extends into the outer surface and around the expandable reservoir axis C1 proximate to each of the first and second opening 302 and 304. When pressure is directed to the passage 306, the portion of the expandable reservoir 104 between the grooves can more readily expand radially outward, relative to the portion of the of the expandable reservoir 104 between the groove and the first and second opening 302 and 304. In some aspects, the alignment feature 310 can be a marking on an inner and/or outer surface of the expandable reservoir 104 to permit observation of the position of the expandable reservoir 104 relative to the housing 102.

The expandable reservoir 104 can include a restraining mechanism that resists radial expansion. The restraining mechanism can be a wire can extend along the expandable reservoir between the first opening 302 and the second opening 304. In some embodiments, the restraining mechanism can be a material having a lattice or mesh shape that extends along the outer surface of the expandable reservoir 104. In another embodiment, the restraining mechanism can be a tubular structure that extends along the outer surface of the expandable reservoir 104.

In some embodiments of the present disclosure, the pressure spike absorbing system 100 includes a spring or lever that can resist radial expansion of the expandable reservoir 104. For example, a spring or lever can extend from the inner surface 124 of the housing toward the expandable reservoir 104. When the expandable reservoir 104 is in the expanded orientation, an outer surface of the expandable reservoir 104 can engage against the spring or lever. The force of the spring or lever against the expandable reservoir 104 could direct the expandable reservoir 104 radially inward, thereby causing the fluid to be directed out of the passage 306.

Figure 5:
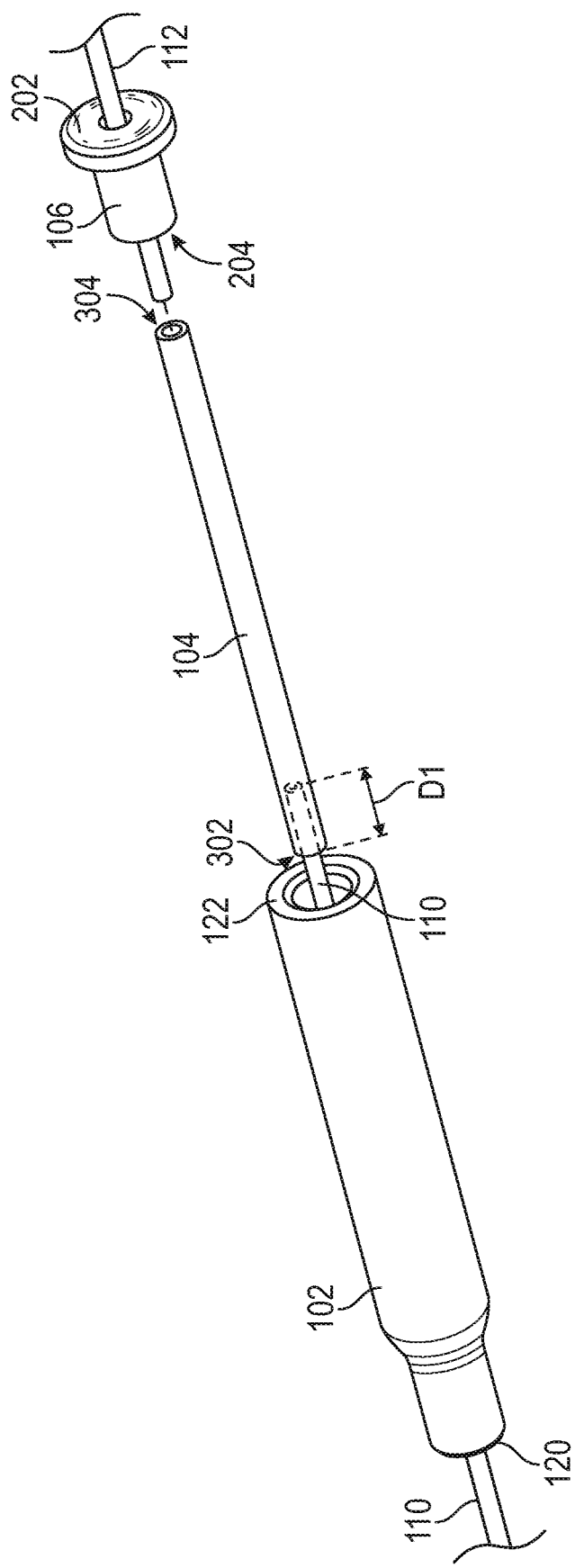
FIG. 5 is an exploded view of a pressure spike absorbing system and tubing, according to some embodiments.

Referring to FIG. 5, an exploded view of the pressure spike absorbing system 100 is illustrated. It should be understood that the following description illustrates assembly and cooperation between portions of the pressure spike absorbing system 100. Accordingly, assembly of the pressure spike absorbing system 100 can include any of the following description, in any variation or sequence.

The pressure spike absorbing system 100 can be coupled with an existing section of IV tubing or fluid delivery system. For example, the tubing can be cut to form a first portion of tubing 110 and a second portion of tubing 112. An end of the first and second portion of tubing 110 and 112 can then be coupled to the pressure spike absorbing system 100. In some embodiments of the present disclosure, the pressure spike absorbing system 100 can be coupled with IV tubing, for example, as a portion of an IV set or fluid delivery system.

To couple the pressure spike absorbing system 100 with tubing, the tubing 110 is inserted through the housing 102. The tubing 110 can be inserted through the housing 102 from the first portion 120 toward the second portion 122 of the housing. When inserted through the housing 102, an end portion of the tubing 110 is moved through the tubing passage 132, the first retaining bore 128, and the cavity 126. When the end portion of the tubing 110 extends through the second portion 122 of the housing, the tubing 110 can be coupled to the expandable reservoir 104.

The tubing 110 can be coupled to the expandable reservoir 104 by inserting the end portion of the tubing 110 through the first opening 302 of the expandable reservoir. The tubing 110 can be moved through the first opening 302 and into the passage 306 so that the outer surface of the tubing 110 extends along the inner surface of the expandable reservoir 104. A portion of the tubing 110 within the passage 306 is identified in broken line in FIG. 5. The end portion of the tubing 110 extends a distance D1 from the first opening 302 of the expandable reservoir.

Another portion of tubing 112 is inserted through the cap 106. The tubing 112 is inserted through the cap 106 by moving the end portion of the tubing 112 through the tubing passage 210 and second retaining bore 208, from the first end portion 202 toward the second end portion 204. When the tubing 112 extends through the second end portion 204 of the cap, the tubing 112 can be coupled to the expandable reservoir 104.

The tubing 112 can be coupled to the expandable reservoir 104 by inserting the end portion of the tubing 112 through the second opening 304 of the expandable reservoir. The tubing 112 can be moved through the second opening 304 and into the passage 306 so that the outer surface of the tubing 112 extends along the inner surface of the expandable reservoir 104. Like the portion of tubing 110 inserted through the first opening 302, the portion of tubing 112 can be extended a distance D1 into the passage 306.

The cap 106 can be moved toward the expandable reservoir 104 so that a portion of the expandable reservoir, adjacent to the second opening 304, is positioned within the second retaining bore 208 and the second opening 304 of the expandable reservoir is aligned with the second tubing passage 210.

The expandable reservoir 104 and a portion of the cap 106 can be moved into the cavity 126 of the housing so that a portion of the expandable reservoir adjacent to the first opening 302 is positioned within the first retaining bore 128 and the first opening 302 is aligned with the first tubing passage 132. When the cap 106 is coupled with the housing 102, the expandable reservoir 104 extends between the first retaining bore 128 and the second retaining bore 208.

In some embodiments of the present disclosure, the expandable reservoir 104 can first be inserted into the housing 102, and then the cap 106 coupled with the housing. When the cap 106 is coupled with the housing 102, the second end portion 204 of the cap is inserted into the housing 102, a portion of the expandable reservoir 104 is received into the second retaining bore 208.

Figure 6A:
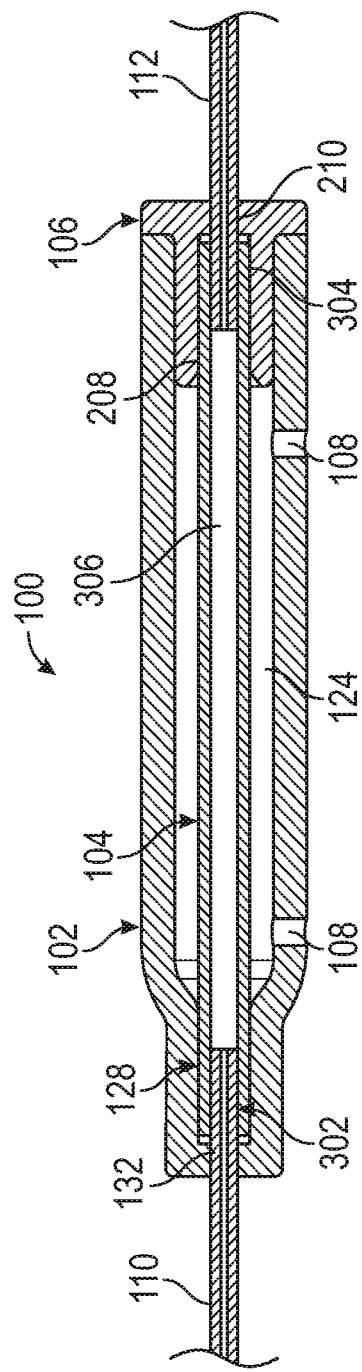
FIGS. 6A and 6B are cross-sectional views of a pressure spike absorbing system coupled to tubing, according to some embodiments.
Figure 6B:
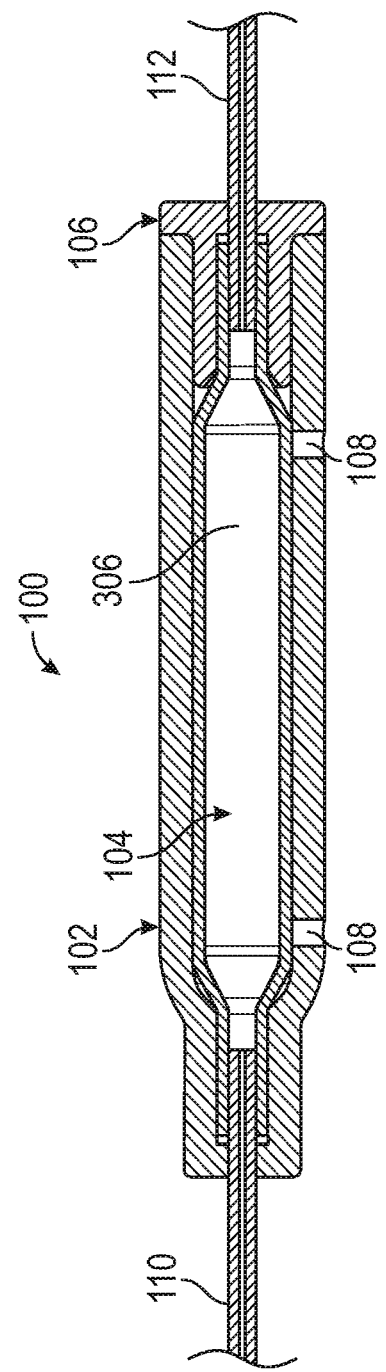

Referring to FIGS. 6A and 6B, cross-sectional views of a pressure spike absorbing system 100 are illustrated. FIG. 6A illustrates an expandable reservoir 104 in an unrestrained orientation, and FIG. 6B illustrates an expandable reservoir 104 in an expanded orientation.

In the unrestrained orientation, a portion of the expandable reservoir 104, adjacent to the first opening 302 is positioned within the first retaining bore 128, and the first opening 302 is aligned with the first tubing passage 132. A portion of the tubing 110 extends through the first tubing passage 132 and is coupled with the first opening 302 of the expandable reservoir.

Another portion of the expandable reservoir 104, adjacent to the second opening 304, is coupled with the cap 106. The another portion of the expandable reservoir is coupled with the cap 106 so that the second opening 304 is aligned with the second tubing passage 210. A portion of the tubing 112 extends through the second tubing passage 210 and is coupled with the second opening 304 of the expandable reservoir.

The outer surface of the expandable reservoir 104 and the inner surface 124 of the housing are spaced apart or separated to permit the expandable reservoir 104 to move, i.e., expand, toward the inner surface of the housing. The space between the outer surface of the expandable reservoir 104 and the inner surface 124 of the housing define a capacity of the pressure spike absorbing system 100. The vents 108 of the housing permit a gas to be directed out of the housing 102 when the expandable reservoir 104 expands, and a gas to be drawn into the housing 102 when the expandable reservoir 104 moves toward the unrestrained orientation.

When coupled with the tubing of an IV set, or other fluid delivery system, the expandable reservoir 104 can deform to relieve pressure and resistance from other portions of the IV set or system. For example, when a fluid is injected into the IV set, the fluid is not immediately injected into the patient; thus, pressure is increased within the IV set. The increase in fluid pressure can act upon portions of the IV set having the least resistance. In some instances, the increase in pressure causes the IV set to become damaged and leak, and can cause resistance to the force injecting the fluid into the IV set.

Because the expandable reservoir can provide less resistance, relative to other portions of the IV set, the expandable reservoir deforms or moves to an expanded orientation to relieve the pressure, as illustrated in FIG. 6B. As the expandable reservoir deforms the volume of the passage 306 increases and permits the fluid to be accommodated therein. By deforming to accommodate the fluid, pressure is relieved or redirected from the other portions of the IV set, which may otherwise become damaged. Further, deformation of the expandable reservoir 104 permits the fluid to be injected into the IV set with less resistance.

In an expanded orientation, a force of the expandable reservoir 104 is directed against the fluid within the passage 306; the force urges the expandable reservoir 104 toward the unrestrained orientation. For example, a force of the expandable reservoir 104 can be directed toward the expandable reservoir axis C1.

When pressure is no longer directed into the expandable reservoir 104, or the force of the expandable reservoir 104 is greater than a force of the fluid engaged against the passage 306, the expandable reservoir 104 can move toward the unrestrained orientation. When the expandable reservoir 104 moves toward the unrestrained orientation, the volume of the passage 306 becomes smaller, thereby directing the fluid out of the expandable reservoir 104.

Figure 7:
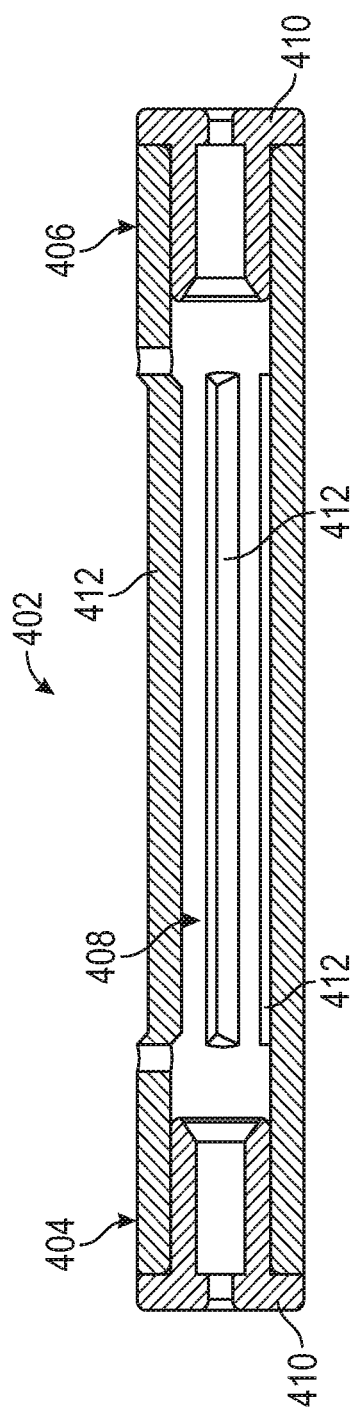
FIG. 7 is a cross-sectional view of another embodiment of a housing of a pressure spike absorbing system and IV tubing, according to some embodiments.
Figure 8:
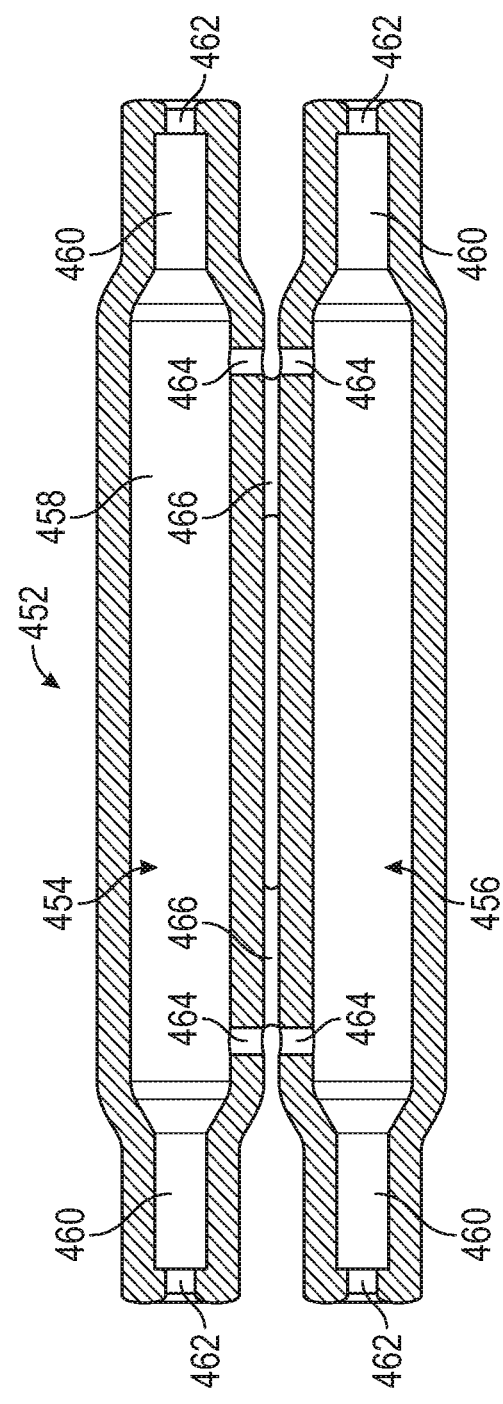
FIG. 8 is a cross-sectional view of another embodiment of a housing of a pressure spike absorbing system and IV tubing, according to some embodiments.

In embodiments of the present disclosure, the pressure spike absorbing system 100 can include any of the features, or any combination of features, described in the present disclosure. Referring to FIGS. 7 and 8, embodiments of a housing having features described in the present disclosure are illustrated.

FIG. 7 illustrates a cross-sectional view of a housing 402 having a first portion 404 and a second portion 406, and a cavity 408 that extends through the first and second portions. Each of the first portion 404 and the second portion 406 include a cap 410 coupled thereto.

The cavity 408 can reduce manufacturing complexity by limiting variations in shape and/or cross-sectional of the passage through the housing 402. Further, the housing 402 can permit a broader manufacturing tolerance, because critical sizing tolerances can be limited to the cap 410.

In some embodiments, the housing 402 can include an opening 412 that extends between the inner and outer surface of the housing 402. The opening 412 can be an elongated passage that extends between the first portion 404 and the second portion 406. In some embodiments of the present application, a portion of the housing 402, between the first portion 404 and the second portion 406, includes a mesh or lattice structure comprising a plurality of openings.

The opening 412 can permit ventilation of the cavity 408. In some aspects of the present disclosure, the opening 412 permits observation of the cavity and/or the expandable reservoir. For example, the opening 412 can permit observation and a determination of whether the expandable reservoir is in a unrestrained or expanded orientation.

In some embodiments, the opening 412 can function like a window and can include a transparent pane to resist movement of an object through the opening 412, yet can permit observation into the housing. In aspects of the present disclosure, any portion, or the entirety of the pressure spike absorbing system can be formed with a transparent material to permit observation into the cavity.

In some embodiments, the pressure spike absorbing system is modular or modifiable. Because any of the housing, the cap of the first portion 404, and the cap of the second portion 406, may be interchangeable or modular, the pressure spike absorbing system can be configured for use with different pressure and/or volume capacities, and/or for use with a variety of expandable reservoirs and IV tubing. For example, the cap of the first portion 404 can be selected to permit a first IV tubing having a first cross-sectional diameter to be moved therethrough. A cap of the second portion 406 can be selected to permit a second IV tubing having a second cross-sectional diameter, different than the first cross-sectional diameter, to be moved therethrough. Thus, the pressure spike absorbing system can be used to transition a portion of the IV set from an IV tubing having a first cross-sectional diameter to an IV tubing having a second cross-sectional diameter.

FIG. 8 illustrates a housing 452 having more than one portion, which can be coupled together. The housing 452 can have a first portion 454 and a second portion 456, which can be coupled together to form any of a cavity, a retaining bore, a tubing passage, and vent passage. In some embodiments, any of the first portion 454 and the second portion 456 form a portion of a cavity 458, a portion of a retaining bore 460, a portion of a tubing passage 462, and a portion of a vent passage 464.

The first portion 454 and the second portion 456 of the housing can be coupled together using any fastening or joining method or mechanism. The first and second portions can include a complimentary pin and pocket, or snap and pawl. The first and second portions can be joined together with an adhesive or welding. In some embodiments, a retainer, such as a band, can extend over or around an outer surface of the first portion 454 and the second portion 456 of the housing. The first portion 454 and the second portion 456 of the housing can be coupled together by a living hinge 466, which permits movement of the first portion 454 relative to the second portion 456.

The pressure spike absorbing system having a housing 452 with a first portion 454 and a second portion 456 can be assembled by first coupling an expandable reservoir between portions of IV tubing. The expandable reservoir can then be positioned within a portion of the cavity 458 with a first portion of the expandable reservoir positioned in a portion of a retaining bore 460 so that a first portion of the tubing extends through a first tubing passage 462. A second portion of the expandable reservoir is positioned in a portion of another retaining bore 460 so that second portion of the tubing extends through another tubing passage 462. The first and second portions of the housing can then be coupled together to enclose the expandable reservoir within the cavity 458. The first and second portions of the housing can be coupled together by moving, or rotating, the first portion 454 of the housing toward the second portion 456 of the housing.

The pressure spike absorbing system can include a flow control valve to resist movement of a fluid relative to the pressure spike absorbing system. The flow control valve can permit fluid to move from an access port of the IV set toward the pressure spike absorbing system, and prevent the fluid from moving from the pressure spike absorbing system toward the access port. The flow control valve can resist movement of a fluid toward the access port when the expandable reservoir moves from an expanded orientation toward an unrestrained orientation. By resisting movement of fluid toward the access port, the fluid is directed toward the patient.

Figure 9:
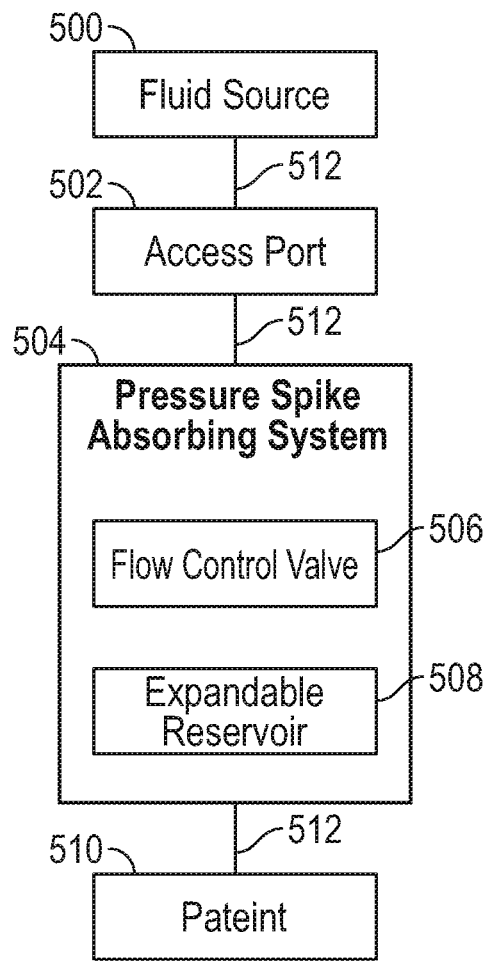
FIGS. 9 and 10 are diagrams of fluid delivery systems having a pressure spike absorbing system, according to some embodiments.
Figure 10:
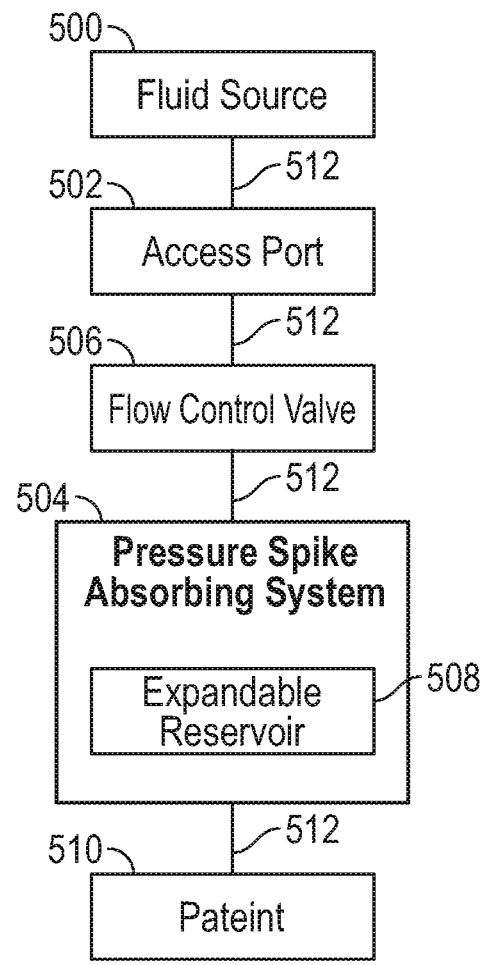

Referring to FIGS. 9 and 10, fluid delivery systems having a flow control valve are illustrated. The fluid delivery systems can include a fluid source 500, such as a medicament bag, an access port 502, and a pressure spike absorbing system 504. The fluid source 500, access port 502, and pressure spike absorbing system 504, can be fluidly coupled together and to a patient 510 by tubing 512.

Referring to FIG. 9, embodiments of a pressure spike absorbing system 504 can include a flow control valve 506 and an expandable reservoir 508. The flow control valve 506 can be incorporate into any of the housing and the expandable reservoir of the pressure spike absorbing system 504. For example, the flow control valve can be fluidly coupled with the tubing passage and/or the retaining bore at a first portion of the housing. When a fluid is directed from the fluid source 500 or access port 502, toward the pressure spike absorbing system 504, the fluid moves through the flow control valve 506 and into the passage of the expandable reservoir 508. When the expandable reservoir 508 moves toward the unrestrained orientation, the flow control valve 506 resists movement of the fluid in a direction from the expandable reservoir 508 toward the access port 502. Thus, the fluid moves toward the patient 510.

Referring to FIG. 10, the flow control valve 506 can be coupled to the fluid delivery system, between the access port 502 and the pressure spike absorbing system 504. For example, the flow control valve 506 can be fluidly coupled to the tubing 512 between the access port 502 and the pressure spike absorbing system 504. When a fluid is directed from the fluid source 500 or access port 502, toward the pressure spike absorbing system 504, the fluid moves through the flow control valve 506 and into the pressure spike absorbing system 504. When the expandable reservoir 508 moves toward the unrestrained orientation, the flow control valve 506 resists movement of the fluid in a direction from the pressure spike absorbing system 504 toward the access port 502. Thus, the fluid moves toward the patient 510.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A pressure spike absorbing system, comprising: a housing comprising a cavity, and a first tubing passage that extends from the cavity through a first portion of the housing to an outer surface of the housing; a cap coupled to a second portion of the housing, the cap comprising a second tubing passage that extends from the cavity through an outer surface of the cap; and an expandable reservoir comprising a passage that extends between a first opening and a second opening, wherein the expandable reservoir is positioned within the cavity with the first opening aligned with the first tubing passage and the second opening aligned with the second tubing passage.

Clause 2. The pressure spike absorbing system of Clause 1, wherein the housing comprises a first retaining bore extending from the cavity toward the first tubing passage, and the cap comprises a second retaining bore extending from the cavity toward the second tubing passage.

Clause 3. The pressure spike absorbing system of Clause 2, wherein a first portion of the expandable reservoir, comprising the first opening, is positioned in the first retaining bore, a second portion of the expandable reservoir, comprising the second opening, is positioned in the second retaining bore, and a third portion of the expandable reservoir, between the first and second portions, is positioned within the cavity.

Clause 4. The pressure spike absorbing system of Clause 1, wherein the cavity extends through the second portion of the housing toward the first portion of the housing.

Clause 5. The pressure spike absorbing system of Clause 1, wherein an inner surface of the housing comprises a cross-sectional width that tapers from the cavity toward the first tubing passage.

Clause 6. The pressure spike absorbing system of Clause 1, wherein an inner surface of the cap comprises a cross-sectional width that tapers from the cavity toward the second tubing passage.

Clause 7. The pressure spike absorbing system of Clause 1, wherein the housing comprises a ventilation passage that extends from the cavity to the outer surface of the housing.

Clause 8. The pressure spike absorbing system of Clause 1, wherein the cap comprises a first end portion and a second end portion, and wherein the second end portion is positioned in the cavity of the housing.

Clause 9. The pressure spike absorbing system of Clause 1, comprising a flow control valve fluidly coupled to the expandable reservoir.

Clause 10. A pressure spike absorbing system, comprising: an intravenous tubing having an access port and an outlet port; a housing comprising a cavity, a first tubing passage that extends from the cavity through a first portion of the housing, and a second tubing passage that extends from the cavity through a second portion of the housing; and an expandable reservoir comprising a first opening, a second opening and a passage that extends between the first and second openings, wherein the expandable reservoir is positioned within the cavity and fluidly coupled with the intravenous tubing between the access port and the outlet port, wherein, when a fluid is injected through the access port, the fluid is directed into the passage to move the expandable reservoir from an unrestrained orientation toward an expanded orientation.

Clause 11. The pressure spike absorbing system of Clause 10, wherein an outer surface of the expandable reservoir is spaced apart from an inner surface of the housing in the unrestrained orientation.

Clause 12. The pressure spike absorbing system of Clause 10, wherein an outer surface of the expandable reservoir is engaged against an inner surface of the housing in the expanded orientation.

Clause 13. The pressure spike absorbing system of Clause 10, wherein when the expandable reservoir moves from the expanded orientation toward the unrestrained orientation, the fluid is directed from the passage toward the outlet port.

Clause 14. The pressure spike absorbing system of Clause 10, comprising a first retaining bore extending between the cavity and the first tubing passage, and a second retaining bore extending between the cavity and the second tubing passage.

Clause 15. The pressure spike absorbing system of Clause 14, wherein in the unrestrained orientation and the expanded orientation, a first portion of the expandable reservoir, comprising the first opening, is positioned in the first retaining bore, a second portion of the expandable reservoir, comprising the second opening, is positioned in the second retaining bore, and a third portion of the expandable reservoir, between the first and second portions, is positioned within the cavity.

Clause 16. The pressure spike absorbing system of Clause 14, comprising a cap having a first end portion, a second end portion, wherein the second retaining bore, and the second tubing passage, extend through the cap.

Clause 17. The pressure spike absorbing system of Clause 15, wherein the second end portion is configured to extend into the cavity of the housing.

Clause 18. The pressure spike absorbing system of Clause 10, wherein the passage of the expandable reservoir comprises a first volume in the unrestrained orientation, and a second volume, greater than the first volume, in the expanded orientation.

Clause 19. The pressure spike absorbing system of Clause 10, comprising a flow control valve coupled between the access port and the expandable reservoir, wherein the flow control valve resists movement of a fluid from the expandable reservoir toward the access port.

Clause 20. The pressure spike absorbing system of Clause 10, wherein the housing comprises a ventilation passage that extends from the cavity to an outer surface of the housing, the ventilation passage configured to permit a gas to move out of the cavity when the expandable reservoir moves from the unrestrained orientation toward the expanded orientation, and a gas to move into the cavity when the expandable reservoir moves from the expanded orientation toward the unrestrained orientation.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

In one or more aspects, the terms "about," "substantially," and "approximately" may provide an industry-accepted tolerance for their corresponding terms and/or relativity between items.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A pressure spike absorbing system, comprising:
    a housing comprising an inner surface forming a cavity, a ventilation passage that extends from the cavity to an outer surface of the housing, a first retaining bore, and a first tubing passage that extends from the cavity through a first portion of the housing, from the first retaining bore to the outer surface of the housing, wherein the inner surface of the housing comprises a cross-sectional width that tapers from the cavity toward the first retaining bore, and the ventilation passage is configured to permit a gas to move into and out of the cavity through the ventilation passage;
    a cap coupled to a second portion of the housing, the cap comprising a second retaining bore and a second tubing passage, wherein the second tubing passage extends from the second retaining bore to an outer surface of the cap; and
    an expandable reservoir comprising a first end having a first opening, a second end having a second opening, and an inner surface forming a passage that extends between the first and second openings, wherein the expandable reservoir is positioned within the cavity such that (i) the first end of the expandable reservoir extends within the first retaining bore such that a first tubing can be inserted into the first opening of the expandable reservoir to engage against the inner surface of the expandable reservoir at the first end thereof, and (ii) the second end of the expandable reservoir extends within the second retaining bore such that a second tubing can be inserted into the second opening of the expandable reservoir to engage against the inner surface of the expandable reservoir at the second end thereof.

2. The pressure spike absorbing system of claim 1, wherein the cavity extends through the second portion of the housing toward the first portion of the housing.

3. The pressure spike absorbing system of claim 1, wherein an inner surface of the cap comprises a cross-sectional width that tapers from the cavity toward the second tubing passage.

4. The pressure spike absorbing system of claim 1, wherein the cap comprises a first end portion and a second end portion, and wherein the second end portion is positioned in the cavity of the housing.

5. The pressure spike absorbing system of claim 1, comprising a flow control valve fluidly coupled to the expandable reservoir.

6. A pressure spike absorbing system, comprising:
    a first tubing end portion and a second tubing end portion;
    a housing comprising a cavity, a ventilation passage that extends from the cavity to an outer surface of the housing, a first tubing passage that extends through a first portion of the housing, a first retaining bore extending from the cavity to the first tubing passage, a second tubing passage that extends through a second portion of the housing, and a second retaining bore extending from the cavity to the second tubing passage, wherein an inner cross-sectional width of the housing tapers from the cavity toward the first retaining bore; and
    an expandable reservoir comprising a first end having a first opening, a second end having a second opening, and a passage that extends between the first and second openings, wherein the expandable reservoir is positioned within the cavity such that the first end of the expandable reservoir extends within the first retaining bore, and the second end of the expandable reservoir extends within the second retaining bore, and wherein (i) the first tubing end portion extends through the first tubing passage and the first opening of the expandable reservoir to engage against an inner surface at the first end of the expandable reservoir, and (ii) the second tubing end portion extends through the second tubing passage and the second opening of the expandable reservoir to engage against the inner surface at the second end of the expandable reservoir,
    wherein, when a fluid is injected through the first tubing end portion, the fluid is directed into the passage to move the expandable reservoir from an unrestrained orientation toward an expanded orientation.

7. The pressure spike absorbing system of claim 6, wherein an outer surface of the expandable reservoir is spaced apart from an inner surface of the housing in the unrestrained orientation.

8. The pressure spike absorbing system of claim 6, wherein an outer surface of the expandable reservoir is engaged against an inner surface of the housing in the expanded orientation.

9. The pressure spike absorbing system of claim 6, wherein when the expandable reservoir moves from the expanded orientation toward the unrestrained orientation, the fluid is directed from the passage toward the second tubing end portion.

10. The pressure spike absorbing system of claim 6, comprising a cap having a first end portion, a second end portion, wherein the second retaining bore and the second tubing passage extend through the cap.

11. The pressure spike absorbing system of claim 10, wherein the second end portion is configured to extend into the cavity of the housing.

12. The pressure spike absorbing system of claim 6, wherein the passage of the expandable reservoir comprises a first volume in the unrestrained orientation, and a second volume, greater than the first volume, in the expanded orientation.

13. The pressure spike absorbing system of claim 6, comprising a flow control valve coupled between the first tubing end portion and the expandable reservoir, wherein the flow control valve resists movement of a fluid from the expandable reservoir toward the first tubing end portion.

14. The pressure spike absorbing system of claim 6, wherein the ventilation passage is configured to permit a gas to move out of the cavity when the expandable reservoir moves from the unrestrained orientation toward the expanded orientation, and to permit a gas to move into the cavity when the expandable reservoir moves from the expanded orientation toward the unrestrained orientation.

15. A pressure spike absorbing system, comprising:

a housing comprising a cavity, a first retaining bore that extends from the cavity toward a first portion of the housing, a first tubing passage that extends from the first retaining bore through the first portion of the housing, a second retaining bore that extends from the cavity toward a second portion of the housing, and a second tubing passage that extends from the second retaining bore through the second portion of the housing, wherein an inner cross-sectional width of the housing tapers from the cavity toward the first retaining bore;

an expandable reservoir comprising an inner surface forming a passage that extends between a first opening at a first end of the expandable reservoir and a second opening at a second end of the expandable reservoir, wherein the expandable reservoir is positioned within the cavity such that the first end of the expandable reservoir extends within the first retaining bore, and the second end of the expandable reservoir extends within the second retaining bore; and an intravenous tubing having an end portion extending through any of the first or second tubing passages such that an outer surface of the intravenous tubing engages against the inner surface of the expandable reservoir along the respective one of the first or second retaining bores.

16. The pressure spike absorbing system of claim 15, wherein the housing comprises a ventilation passage that extends from the cavity to an outer surface of the housing.

17. The pressure spike absorbing system of claim 15, wherein the intravenous tubing is coupled to the expandable reservoir by an interference fit.

18. The pressure spike absorbing system of claim 15, wherein the cross-sectional width tapers from the cavity toward the second retaining bore.

* * * * *